United States Patent [19]

Gerdes

[11] Patent Number: 4,621,518
[45] Date of Patent: Nov. 11, 1986

[54] ANALYZER FOR WATER IN GASES BY ACCUMULATE-DESORB-INJECT METHOD

[75] Inventor: Walter F. Gerdes, Lake Jackson, Tex.

[73] Assignee: The Dow Chemical Company, Midland, Mich.

[21] Appl. No.: 747,537

[22] Filed: Jun. 21, 1985

[51] Int. Cl.$^4$ ............................................. G01N 30/00
[52] U.S. Cl. ........................................................ 73/29
[58] Field of Search ..................... 73/29, 23.1, 1 G; 55/387, 18, 29, 35

[56] References Cited

U.S. PATENT DOCUMENTS

| | | | |
|---|---|---|---|
| 3,188,283 | 6/1965 | Cole | 204/129 |
| 3,257,609 | 6/1966 | Sanford et al. | 73/23 |
| 3,263,493 | 8/1966 | Davidson | 73/23.1 |
| 3,355,367 | 8/1964 | Marsh | 204/1 R |
| 3,405,550 | 10/1968 | Bloch | 73/23.1 |
| 3,807,217 | 4/1974 | Wilkins et al. | 73/23.1 |
| 3,897,679 | 8/1975 | Guild | 73/23.1 |
| 4,359,891 | 11/1982 | Ahlstrom, Jr. et al. | 73/23.1 |
| 4,391,616 | 7/1983 | Imamura | 55/35 |

FOREIGN PATENT DOCUMENTS 0075145 4/1984 Japan ............................ 73/29

Primary Examiner—Stephen A. Kreitman
Attorney, Agent, or Firm—M. W. Barrow

[57] ABSTRACT

A method and apparatus for measuring very low levels of moisture in gases and vapors including an absorption column packed with fibers to selectively absorb the moisture. Preferably, the column is loosely packed with glass fibers. The moisture is desorbed from the column with a carrier gas that is passed through a moisture analyzer, preferably a $P_2O_5$ hygrometer.

9 Claims, 2 Drawing Figures

ANALYZER FOR WATER IN GASES BY ACCUMULATE-DESORB-INJECT METHOD

FIELD OF THE INVENTION

This invention relates generally to chromatograph systems and, more particularly, to the use of a combined chromatograph-hygrometer system for moisture analysis of gas samples.

BACKGROUND OF THE INVENTION

The presence of water in small quantities in gaseous hydrocarbons is harmful to industrial processes and the monitoring of moisture content is necessary to assure proper results. The aluminum oxide hygrometer is very good for measuring very low levels of moisture in gases and some liquids if the sample is not harmful toward aluminum or aluminum oxide. The $P_2O_5$ hygrometer is somewhat less sensitive but very useful for many more harmful gas samples encountered in chemical plants. However, some samples are disruptive of the $P_2O_5$ hygrometer. HCl in concentration above 1% gives a background reading because the HCl is partially electrolyzed. For such samples that contain very low ranges of moisture, the signal from the $P_2O_5$ hygrometer is low and subject to considerable uncertainty. The levels of moisture which are of concern generally are in the range of 2 to 50 parts per million (ppm).

U.S. Pat. No. 3,257,609 discloses the use of an adsorption column to selectively separate and accumulate moisture from gaseous hydrocarbon samples followed by desorption and analysis with a hygrometer. U.S. Pat. No. 3,257,609 specifically teaches the use of polyethylene and propropylene glycols on Chromosorb (an agglomerated diatomaceous earth) to adsorb moisture from a process sample. Desorption is accomplished by passing an electrical current through the column to raise the temperature.

U.S. Pat. Nos. 3,263,493 and 3,335,367 disclose the use of gas chromatography columns to separate moisture from gaseous hydrocarbon samples prior to the analysis of the moisture laden fraction with a hygrometer. The hygrometer is conditioned with dry carrier gas when the moisture laden fraction of the sample is not exiting the column.

The use of chromatography columns to accumulate a volume of sample requires knowledge of the flow through the accumulator during the load interval. Thus, sample flow rate and load time must be controlled.

SUMMARY OF THE INVENTION

The invention provides a method and apparatus for measuring low ppm moisture content of gases or vapors, including corrosive or reactive gases which are not handled by known methods of analyzing for water. The method comprises accumulating the water from a rather large volume of sample gas over a period of a few seconds to many minutes using a column loosely packed with fibers, then quickly desorbing the accumulated water with a stream of very dry carrier gas, such as nitrogen, by rapidly heating the column, and then measuring the moisture contained in the carrier gas with a $P_2O_5$ electrolytic hygrometer.

The moisture content of the sample is interpreted from the peak height or area of the resulting current peak relative to the volume of sample gas from which the water producing it was accumulated. A calibration factor must be determined by running samples of known water content.

The following presents a specific embodiment of the invention and a description thereof in accordance with the accompanying drawings, in which:

FIG. 1 illustrates schematically a moisture analyzer in accordance with the subject invention; and FIG. 2 illustrates the change in flow patterns from FIG. 1 resulting from the movement of valves.

DESCRIPTION OF A SPECIFIC EMBODIMENT

Figure 1:
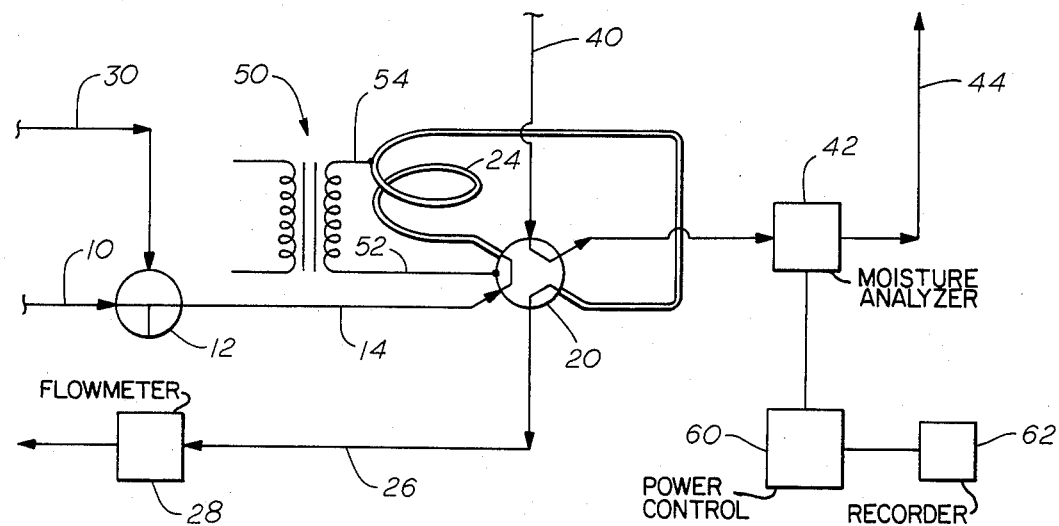

As shown in FIG. 1, sample 10 of a gas stream that contains a low level of moisture is in fluid communication with a 3-way solenoid valve 12. When the valve 12 is positioned as shown in FIG. 1, the gas sample 10 flows through line 14 into a 6-port valve 20. The 6-port valve has an inner core that rotates 60°. In the configuration of valve 20 shown in FIG. 1, the gas sample 10 passes through the valve 20, through a column loosely packed with fibers 24, through the 6-port valve 20 once again, through line 26, and through a flow measuring device 28 before exiting the apparatus. The flow measuring device 28 can be an ordinary rotometer because the accuracy of this measurement is not critical given other variables. The gas sample 10 can be passed through the column 24 as long as the fibers in the column adsorb and accumulate most of the moisture from the sample.

The recommended volume of the gas sample that can be passed through the column depends upon the dimensions of the column, specific method for packing the column, and the moisture content of the gas vapor stream. A volume of 3 liters was preferred for a 4 foot column made of ⅛ inch diameter thin wall stainless steel tubing and loosely packed with a single strand of glass fiber yarn for a gas sample containing about 40 ppm of moisture. The flow rate of the gas sample for the preceding column can range between 10 ml/min. to about 100 ml/min.

Preferably, the column 24 is packed with fibers that have large surface areas per unit volume, have low to moderate specific heat coefficients, are stable against thermal degredation, and are capable of rapid water desorption by increased temperature. Glass fibers satisfy all of the requirements and are inexpensive. Other fibers, such as graphite, may be better than glass for some harmful samples although more expensive.

Figure 2:
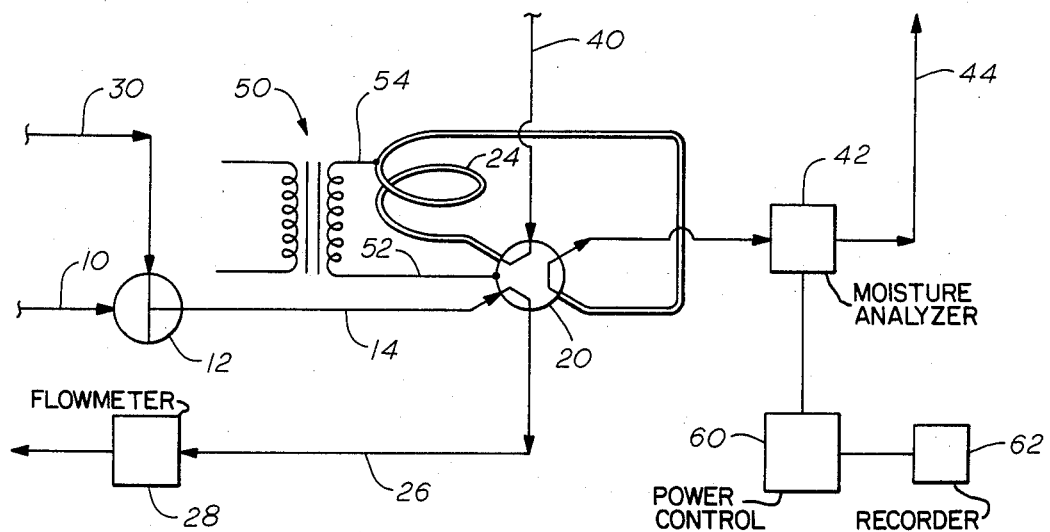

At the end of a predetermined period for accumulating moisture from the gas sample 10, a timer (not shown) switches the 3-way solenoid valve 12 to the configuration shown in FIG. 2. A purge gas 30, preferably a dry inert gas such as nitrogen, then passes through column 24 for about 15 to 30 seconds to purge the gas sample from the column. The length of the purge is controlled with the timer (not shown) by switching the configuration of the 6-port valve 20 at a predetermined time. The change in the configuration of valve 20 is shown in FIG. 2 and is discussed below.

While the 6-port valve 20 remains in the configuration shown in FIG. 1, a carrier gas 40, preferably a dry inert gas such as nitrogen, passes through the valve 20, a moisture analyzer 42, preferably a $P_2O_5$ hygrometer, and a vent to the atmosphere 44.

While the gas sample 10 or the purge gas 30 are flowing through the column 24, the column 24 is kept at ambient temperature or else heated within an oven (not shown) to a temperature of from about 40° to about 75° C. An oven temperature of from about 60° to about 75°

C. appears optimum for the glass fiber packed column described above. Lower temperatures allow water to accumulate on all the surfaces of the described column causing problems in the analysis of gas samples having very low levels of moisture. Higher temperatures reduce the adsorption capacity of the glass fiber packing used in the described system.

Following the purge of the column 24 described above, the configuration of valve 20 is altered as shown in FIG. 2. The gas exiting solenoid valve 12, either sample gas 10 or purge gas 30, passes through the 6-port valve 20 and flow meter 28 to the atmosphere. The carrier gas 40 passes through 6-port valve 20, the column 24, and the 6-port valve 20 once again before passing through the moisture analyzer 42 and the vent 44.

When the 6-port valve 20 is switched to the configuration shown in FIG. 2, a heater transformer 50 attached to column 24 is energized and rapidly heats the column 24 to a temperature of from about 260° to about 280° C. by passing an electrical current through the column 24. The heater transformer 50 is conductibly connected to the column 24 by a wire 52 between the heater 50 and the 6-port valve 20 and by a wire 54 between the heater 50 and the center of the column 24. The 6-port valve 20 and the column 24 are conductibly connected at the ends of the column 24 by the use of metal connectors (not shown) to connect the column 24 to the valve 20.

While the 6-port valve 20 remains in the configuration shown in FIG. 2, the carrier gas 40 desorbs the moisture from the column 24 and carries it to the moisture analyzer 42. A power control box 60 works in conjunction with the control timer (not shown) to activate a chart recorder 62 that records the moisture content of the carrier gas 40 now containing the moisture desorbed from the column 24. The control box 60 also periodically activates the chart recorder 62 while the carrier gas 40 is passing directly through the 6-port valve 20 to the moisture analyzer 42 in order to establish a base line.

The moisture content of the gas sample 10 can be calculated from the peak heights recorded by the chart recorder 62. A calibration factor must be determined by running samples of a known moisture content. Thus, a given peak height could be converted to a known volume of moisture from which the moisture content of the sample gas 10 can be calculated using the gas sample flow rate that was set using flow meter 28 and the sampling time to establish the volume of the gas sample.

What is claimed is:

1. A method of measuring the moisture content of gas samples containing low levels of moisture, comprising the sequential steps of:

passing the gas sample through a column loosely packed with fibers for a predetermined period of time to selectively adsorb the moisture;

desorbing the moisture from said column with a carrier gas by rapidly heating said column; and passing said carrier gas containing the desorbed moisture through a moisture analyzer.

2. The method of claim 1 wherein said column is rapidly heated during desorption to a temperature of from about 260° to about 280° C. by passing a current through the column.

3. The method of claim 1 wherein said moisture analyzer is a $P_2O_5$ hygrometer.

4. The method of claim 1 wherein said fibers are glass fibers.

5. An apparatus for measuring the moisture content of gas samples containing low levels of moisture, comprising:

a column loosely packed with fibers;

switching means for:

providing fluid communication sequentially between the inlet of said column and either a gas sample or a carrier gas, whereby the gas sample can be passed through the column for a predetermined time to selectively adsorb moisture and the carrier gas can be passed through the column for a predetermined time to desorb the moisture from the column, and providing fluid communication sequentially between the outlet of said column and either a vent to the atmosphere or a moisture analyzer, whereby said gas sample can be vented from the apparatus after passing through the column and said carrier gas used to desorb the moisture can be sent to the moisture analyzer;

means for quickly heating said column to a predetermined temperature to desorb the moisture while the column is in fluid communication with said carrier gas and said moisture analyzer; and a moisture analyzer, said analyzer being in fluid communication with said column while said carrier gas is being used to desorb the moisture from the column.

6. The apparatus of claim 5, wherein said column is loosely packed with one or more threads of glass fibers.

7. The apparatus of claim 5, wherein the means for quickly heating said column is a heater transformer conductively connected to the column.

8. The apparatus of claim 5, wherein said moisture analyzer is a $P_2O_5$ hygrometer.

9. The apparatus of claim 5, wherein said switching means includes a 6-port rotary valve for placing the inlet of said column in fluid communication with either said gas sample or said carrier gas, for placing said moisture analyzer in fluid communication with either said carrier gas or the outlet of said column, and for placing the outlet of said column in fluid communication with either said vent or said moisture analyzer.

* * * * *